United States Patent
Rasmussen et al.

(10) Patent No.: US 10,662,400 B2
(45) Date of Patent: May 26, 2020

(54) MICROENCAPULATION USING SMALL AMINES

(71) Applicant: Novozymes A/S, Bagsvaerd (DK)

(72) Inventors: Amra Tihic Rasmussen, Bagsvaerd (DE); Kim Bruno Andersen, Vaerloese (DK); Katarina Larson, Malmoe (SE); Lotte Elisabeth Nissen, Lyngby (DK); Martin Noerby, Vaerloese (DK); Ole Simonsen, Soeborg (DK); Tue Rasmussen, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/127,840

(22) PCT Filed: Mar. 25, 2015

(86) PCT No.: PCT/EP2015/056465
§ 371 (c)(1),
(2) Date: Sep. 21, 2016

(87) PCT Pub. No.: WO2015/144784
PCT Pub. Date: Oct. 1, 2015

(65) Prior Publication Data
US 2017/0107461 A1 Apr. 20, 2017

(30) Foreign Application Priority Data

Mar. 25, 2014 (EP) .................... 14161543
May 2, 2014 (WO) ............... PCT/EP2014/059017
Oct. 31, 2014 (EP) .................... 14191322

(51) Int. Cl.
| | | |
|---|---|---|
| C11D 17/00 | (2006.01) | |
| C11D 3/386 | (2006.01) | |
| C12N 9/96 | (2006.01) | |
| C12N 9/98 | (2006.01) | |
| C11D 3/37 | (2006.01) | |
| C11D 11/00 | (2006.01) | |
| C12N 9/20 | (2006.01) | |

(52) U.S. Cl.
CPC ........ *C11D 17/0039* (2013.01); *C11D 3/3723* (2013.01); *C11D 3/38627* (2013.01); *C11D 3/38672* (2013.01); *C11D 11/0017* (2013.01); *C12N 9/20* (2013.01); *C12N 9/96* (2013.01); *C12N 9/98* (2013.01); *C12Y 301/01003* (2013.01)

(58) Field of Classification Search
CPC .... C11D 3/38672; C11D 3/3723; C11D 3/386
See application file for complete search history.

(56) References Cited

U.S. PATENT DOCUMENTS

| | | | | |
|---|---|---|---|---|
| 3,796,634 | A * | 3/1974 | Haynes ................ | C12N 11/08 435/176 |
| 6,242,405 | B1 * | 6/2001 | Lykke .................... | B01J 13/16 435/177 |
| 2010/0078381 | A1 * | 4/2010 | Merchant ........... | B01D 67/0006 210/632 |
| 2012/0322708 | A1 * | 12/2012 | Lant ................... | C11D 3/38636 510/101 |

FOREIGN PATENT DOCUMENTS

| | | | | |
|---|---|---|---|---|
| EP | 0356239 | A2 | 2/1990 | |
| JP | 63137996 | A | 6/1988 | |
| RU | 2690681 | C2 * | 6/2019 | ......... C11D 3/38636 |
| WO | 1992/20771 | A1 | 11/1992 | |
| WO | 1997/24177 | A1 | 7/1997 | |
| WO | 1998/16621 | A2 | 4/1998 | |
| WO | 2006/048166 | A1 | 5/2006 | |

OTHER PUBLICATIONS

Synthesis of poly(diethylenetriamine terephthalamide) and its application as a flame retardant for ABS Xingyou Chen1 • Xufu Cai1 J Therm Anal Calorim (2016) 125:313-320 (Year: 2016).*
Google Patents Translation of RU-2690681-C2 pp. 1-55. Jun. 2019 (Year: 2019).*
Grunwald et al, 1978, Biochem Bipphys Res Comm, vol. 81, No. 2, pp. 565-570.
Ilan et al, 1986, Appl Biochem Biotechnol, vol. 13, No. 3, pp. 221-230.
Poncelet et al, 1994, J Microencapsulation, vol. 11, No. 1, pp. 31-40.

\* cited by examiner

*Primary Examiner* — Vasudevan S Jagannathan
*Assistant Examiner* — Preeti Kumar
(74) *Attorney, Agent, or Firm* — Eric Fechter

(57) ABSTRACT

The present invention provides a microcapsule composition produced by crosslinking of a polybranched polyamine and a small amine, which is used for stabilizing detergent components.

17 Claims, No Drawings
Specification includes a Sequence Listing.

MICROENCAPULATION USING SMALL AMINES

CROSS-REFERENCE TO RELATED APPLICATIONS

This application is a 35 U.S.C. 371 national application of PCT/EP2015/056465 filed Mar. 25, 2015 which claims priority or the benefit under 35 U.S.C. 119 of European application 14161543.5 filed Mar. 25, 2014, PCT/EP2014/059017 filed May 2, 2014 and European application 14191322.8 filed Oct. 31, 2014, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The invention relates to microcapsules used for stabilization of detergent components, such as enzymes.

BACKGROUND

It is known to be desirable to protect enzymes and components having compatibility problems with other components in liquid detergent concentrates. There have been many proposals in the literature to protect the enzyme from the continuous phase of the concentrate and/or water by providing a continuous shell and/or a matrix which is intended to protect the enzyme from the concentrate but to release it when the detergent concentrate is added to water to provide wash water. Examples are given in EP 356,239 and WO 92/20771, and the prior art discussed in those. These, and other known methods, generally involve forming the shell by coacervation.

Unfortunately it is very difficult to select a coacervation polymer and its conditions of use on the one hand, and a polymeric or other core composition on the other, so as to obtain in particles of high specific area the optimum protection and release performance that is required. In general, either the shell is too impermeable to give effective release when required or the shell permits premature release.

Various encapsulation techniques other than coacervation are known for various purposes and one such technique which has been used for other processes is inter facial condensation (IFC) polymerization. IFC encapsulation techniques are generally conducted in oil-in-water dispersions (so that the oil phase becomes the core) but it is also known to conduct IFC encapsulation on a water-in-oil dispersion (so that the water phase becomes the core).

Grunwald et al. "Nylon polyethyleneimine microcapsules for immobilizing multienzymes with soluble dextran-NAD+ for the continuous recycling of the microencapsulated dextran-NAD+", *Biochem and Biophys Res Comm*, vol. 81, 2 (1978), pp. 565-570, discloses preparation of semipermeable nylon polyethyleneimine microcapsules containing a multi-enzyme system of yeast alcohol dehydrogenase (EC 1.1.1.1) and malic dehydrogenase (EC 1.1.1.37) together with a soluble immobilized coenzyme, dextran-NAD+.

Poncelet et al. "Microencapsulation within crosslinked polyetylenimine membranes", *J. Microencapsulation*, vol. 11, 1 (1994), pp. 31-40, discloses a microencapsulation technique involving formation of a PEI membrane, which is particularly suited for immobilization of biocatalysts.

WO 97/24177 describes a liquid detergent concentrate with enzyme containing particles. The particles have a polymer shell formed from a condensation polymer, and contain a core polymer which causes stretching of the polymer shell upon dilution of the detergent concentrate in water. Encapsulated precipitated enzymes are also disclosed.

JP-A-63-137996 describes liquid detergents containing encapsulated materials wherein the encapsulation can be by coacervation or by IFC polymerization. The objective in JP 63-137996 is to include in the core a water-soluble or water absorbent polymer that will swell sufficiently when the detergent is put into wash water to cause rupture of the capsules, with consequential release of the core.

We have found that it is not possible to achieve the desired result using any of the microencapsulation procedures previously described for encapsulating enzymes and components having compatibility problems with other components in liquid detergent concentrates. In practice, either the membrane is generally too permeable to prevent migration of the relatively low molecular weight enzyme through the high specific surface area provided by the membrane, or the membrane is so impermeable and strong that it cannot reliably release the enzyme when the concentrate is added to wash water. The processes are not capable of easy reproducible operation to give the desired combination of properties.

The prior art references have failed to acknowledge the usefulness of microcapsules based on polybranched polyamines, such as PEI, for improving the storage stability of enzymes and other components in detergents, while at the same time being capable of delivering the content of the microcapsule timely in a detergent application.

SUMMARY

In a first aspect, the present invention provides a microcapsule composition, comprising a compound entrapped in a compartment formed by a membrane, which membrane is produced by cross-linking of (a) a polybranched polyamine having a molecular weight of more than 800 Da, and (b) an aliphatic or aromatic amine having a molecular weight of less than 300 Da; wherein the weight ratio of (a)/(b) is in the range of 0.1 to 1000.

In an embodiment, the compound is an enzyme.

In a second aspect, the invention provides a detergent composition, comprising a surfactant and a detergent builder, and the microcapsule composition of the invention.

In other aspects, the invention provides methods for preparing the compositions of the invention, and methods and uses of the compositions of the invention for stabilizing compounds, such as enzymes.

Other aspects and embodiments of the invention are apparent from the description and examples.

DETAILED DESCRIPTION

The inventors of the present invention have found that microcapsules with a membrane made by cross-linking of polybranched polyamines and small aliphatic or aromatic amines are particularly useful for encapsulating and stabilizing detergent enzymes and other compounds in liquid detergent compositions, such as laundry or (automatic) dish wash detergents. We have found that the membrane of the microcapsule is capable of improving the storage stability of the encapsulated enzyme(s) in a liquid detergent composition (as compared to a non-encapsulated enzyme), as demonstrated in Example 1 and 2. The membrane formed by crosslinking the polybranched polyamine and small aliphatic or aromatic amine is capable of separating an enzyme or another compound from, e.g., (anionic) surfactants, or other detergent components causing incompatibility problems, in the detergent.

A critically important parameter when using encapsulated enzymes in detergents is the ability to release the enzyme immediately upon dilution of the detergent in water, as for example in a laundry or dishwash application. The microcapsules of the present invention have excellent properties in this regard, and are capable of quickly releasing the entire encapsulated enzyme.

The microcapsules, as described in the present invention, do not require the presence of a core polymer to be capable of releasing the enzyme, upon dilution in water. Further, the invention does not require the enzyme to be in a precipitated form in the core of the microcapsule, in order to control premature release, as described in WO 97/24177.

We have found, that encapsulating enzymes or other compounds in a microcapsule with a semipermeable membrane of the invention, and having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of the enzyme in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme.

The concept is very efficient in stabilizing enzymes against hostile components in liquid detergents, and vice versa also protects enzyme sensitive/labile components in liquid detergents from enzymes.

Components which are labile to enzyme degradation are increasingly used in detergents due to the, in many cases, high biodegradability of such components.

Cellulases may degrade celluloses and cellulose salts such as carboxymethyl cellulose CMC (and Na-CMC) or microcrystalline cellulose used, e.g., for anti-redeposition of soil, as rheology modifiers and builders.

Amylases may degrade starch and starch derivatives such as e.g. starch based surfactants or carboxylated starch used as builder. Starches can also be used as rheology modifiers or fillers.

Proteases may degrade peptides/proteins or components with peptide/amide bonds, e.g., peptides with detergent properties ("peptergents").

Lipases may degrade components with ester bonds such as lipids, e.g., some types of lipid based or polyester soil release polymers, lipid based surfactants, lipid based structurants or rheology modifiers (like di- and triglyceride structurants, e.g., hydrogenated castor oil and derivatives) and perfumes with ester bonds etc.

Mannanase and Xanthanase may degrade mannan and xanthan type components, like guar gum and xanthan gum, which are used as rheology modifier in detergents.

Pectinases (pectin lyases or pectate lyases) may degrade pectins and pectates (pectic polysaccharides), which can be used, e.g., as rheology modifiers in detergent.

Chitonsanase may degrade chitosan, and xylanases may degrade xylans and xylan surfactants.

The encapsulated compounds may also be enzyme substrates or co-substrates, which are intended to react directly or indirectly with the enzyme, but require separation from the enzyme during storage of the liquid detergent composition. Examples of enzyme substrates or co-substrates include, but are not limited to, hydrogen peroxide or hydrogen peroxide precursors like percarbonates or perborates (substrates of oxidoreductases like peroxidase/haloperoxidase), sugars or polyols for in situ hydrogen peroxide generation (substrates of oxidases), ester substrates like propylene glycol diacetate (substrates of perhydrolase), and laccase/peroxidase mediators.

Also other sensitive/labile compounds can be encapsulated, and thus separated and stabilized against reactive or incompatible compounds. Generally, the microcapsules of the invention can be used to separate at least two mutually reactive or incompatible components/compounds.

The microcapsules may be used for separation of incompatible polymers and/or incompatible components with opposite charge, like cationic polymers or cationic surfactants from anionic polymers or anionic surfactants.

Particularly, by using the microcapsules of the invention, sensitive, chemically or physically incompatible and volatile components of a liquid detergent or cleaning agent can be enclosed so as to be stable during storage and transport, and can be homogeneously dispersed in the liquid detergent or cleaning agent. This ensures, i.a., that the detergent or cleaning agent is available to the consumer with full detergent and cleaning power at the time of use.

In addition to separation of specific incompatible components, the microencapsulation of the invention can also be used to add detergent components at a higher dosage than the detergent solubility allows, or when there is a risk of phase separation during storage. Components like optical brighteners, builders, salts, surfactants, polymers, etc., may be useful to add in concentrations above their solubility in the detergent, or they may phase separate during storage. Other components are useful to add as emulsions (e.g., oil-in-water emulsions), which may not be stable in the detergent during storage—such as emulsions of antifoam oil or perfumes/fragrances. By encapsulating these components or emulsions, the solubility or phase separation problems are confined to the inside (the core, internal phase, compartment) of the microcapsules. Thus, the rest of the liquid detergent composition will not be affected by inhomogeneity due to precipitated solids or phase separation.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsules

The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Use of methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent, or solution thereof, can be mixed by conventional methods used in the art, e.g., by simple mixing or by carefully controlling the flows of the emulsion and the cross-linking agent solution through an in-line mixer.

In some cases curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule according to the invention is a small aqueous sphere with a uniform membrane around it (a compartment formed by the membrane). The material inside the microcapsule (entrapped in the microcapsule) is referred to as the core, internal phase, or fill, whereas the membrane is sometimes called a shell, coating, or wall. The microcapsules of the invention have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes or other compounds, as used in the present invention, may be carried out by interfacial polymerization, wherein the two reactants in a polymerization reaction meet at an interface and react rapidly. The basis of this method is a reaction of a polyamine and a small amine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion

An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favorable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared— it is not formed in situ from other starting materials. To obtain the attractive properties of the invention, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear di-amine will allow one or more primary amine(s) to be introduced at the end of the introduced branch(es). In this context we understand the primary amino group as part of the branch, i.e., the endpoint of the branch. For example, we consider both tris(2-aminoethyl)amine and 1,2,3-propanetriamine as molecules having one branching point. For the invention the polyamine has at least four primary amines. Branching points can be introduced from an aliphatic hydrocarbon chain as in the previously stated examples or from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, we have found that the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

In an embodiment, the reactive amino groups constitute at least 15% of the molecular weight of the polybranched polyamine, such as more than 20%, or more than 25%. Preferably, the molecular weight of the polybranched polyamine is at least 800 Da; more preferably at least 1 kDa, and most preferably at least 1.3 kDa.

In a preferred embodiment, the polybranched polyamine is a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 800 Da; more preferably at least 1 kDa; and most preferably at least 1.3 kDa.

Combinations of different polybranched polyamines may be used for preparing the microcapsule according to the invention.

Small Amine

The microcapsules of the invention are made by using one or more small aliphatic or aromatic amines in the cross-linking reaction forming the membrane of the microcapsules. The small aliphatic or aromatic amines are added with the polybranched polyamines to the aqueous solution used in the cross-linking reaction forming the membrane of the microcapsules.

The small aliphatic or aromatic amines have a molecular weight of less than 500 Da, preferably less than 400 Da, more preferably less than 300 Da, and most preferably less than 250 Da.

The small aliphatic or aromatic amine is preferably substantially water-soluble (when in free base form). Preferably the small amine is an aliphatic amine, more preferably it is an alkylamine with one or more amino groups, such as an ethyleneamine or alkanolamine.

The small aliphatic or aromatic amine may be selected from the group consisting of ethylene diamine, diethylene triamine, triethylene tetraamine, bis(3-aminopropyl)amine, monoethanolamine, diethanolamine, triethanolamine, hexamethylene diamine, diamino benzene, piperazine, and tetraethylene pentamine.

The small amine should be selected to ensure compatibility with the compound entrapped/encapsulated in the microcapsules of the invention.

The small amine may be added in an amount of from 0.1% to 90%, preferably from 0.2% to 90%, more preferably from 0.5% to 90%, even more preferably from 0.5% to 50%, by weight of the total content of small amine and polybranched polyamine, when preparing the microcapsule of the invention.

The weight ratio of: (polybranched polyamine)/(small amine) is in the range of 0.1 to 1000; preferably in the range of 0.1 to 500; more preferably in the range of 0.1 to 250; and most preferably in the range of 1 to 250.

Combinations of different small amines may be used for preparing the microcapsules according to the invention.

Crosslinking Agent

The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is isophthaloyl chloride, terephthaloyl chloride, or trimesoyl chloride.

Enzyme(s)

The microcapsule of the invention may include one or more enzymes suitable for including in laundry or dishwash detergents (detergent enzymes), such as a protease (e.g., subtilisin or metalloprotease), lipase, cutinase, amylase, carbohydrase, cellulase, pectinase, mannanase, arabinase, galactanase, xanthanase (EC 4.2.2.12), xylanase, DNAse, perhydrolase, oxidoreductase (e.g., laccase, peroxidase, peroxygenase and/or haloperoxidase). Preferred detergent enzymes are protease (e.g., subtilisin or metalloprotease), lipase, amylase, lyase, cellulase, pectinase, mannanase, DNAse, perhydrolase, and oxidoreductases (e.g., laccase, peroxidase, peroxygenase and/or haloperoxidase); or combinations thereof. More preferred detergent enzymes are protease (e.g., subtilisin or metalloprotease), lipase, amylase, cellulase, pectinase, and mannanase; or combinations thereof.

The microcapsule may include more than 0.1% of active enzyme protein; preferably more than 0.25%, more preferably more than 0.5%, more preferably more than 1%, more preferably more than 2.5%, more preferably more than 5%, more preferably more than 7.5%, more preferably more than 10%, more preferably more than 12.5%, more preferably more than 15%, even more preferably more than 20%, and most preferably more than 25% of active enzyme protein.

Proteases:

The proteases for use in the present invention are serine proteases, such as subtilisins, metalloproteases and/or trypsin-like proteases. Preferably, the proteases are subtilisins or metalloproteases; more preferably, the proteases are subtilisins.

A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272). Subtilisins include, preferably consist of, the I-S1 and I-S2 sub-groups as defined by Siezen et al., Protein Engng. 4 (1991) 719-737; and Siezen et al., Protein Science 6 (1997) 501-523. Because of the highly conserved structure of the active site of serine proteases, the subtilisin according to the invention may be functionally equivalent to the proposed sub-group designated subtilase by Siezen et al. (supra).

The subtilisin may be of animal, vegetable or microbial origin, including chemically or genetically modified mutants (protein engineered variants), preferably an alkaline microbial subtilisin. Examples of subtilisins are those derived from *Bacillus*, e.g., subtilisin Novo, subtilisin Carlsberg, subtilisin 309, subtilisin 147 and subtilisin BPN', subtilisin 168 (described in WO 89/06279) and Protease PD138 (WO 93/18140). Examples are described in WO 98/020115, WO 01/44452, WO 01/58275, WO 01/58276, WO 03/006602 and WO 04/099401. Examples of trypsin-like proteases are trypsin (e.g., of porcine or bovine origin) and the *Fusarium* protease described in WO 89/06270 and WO 94/25583. Other examples are the variants described in WO 92/19729, WO 88/08028, WO 98/20115, WO 98/20116, WO 98/34946, WO 2000/037599, WO 2011/036263, especially the variants with substitutions in one or more of the following positions: 27, 36, 57, 76, 87, 97, 101, 104, 120, 123, 167, 170, 194, 206, 218, 222, 224, 235, and 274.

The metalloprotease may be of animal, vegetable or microbial origin, including chemically or genetically modified mutants (protein engineered variants), preferably an alkaline microbial metalloprotease. Examples are described in WO 2007/044993, WO 2012/110562 and WO 2008/134343.

Examples of commercially available subtilisins include Kannase™, Everlase™, Relase™, Esperase™, Alcalase™, Durazym™, Savinase™, Ovozyme™, Liquanase™, Coronase™, Polarzyme™, Pyrase™, Pancreatic Trypsin NOVO (PTN), Bio-Feed™ Pro and Clear-Lens™ Pro; Blaze (all available from Novozymes A/S, Bagsvaerd, Denmark). Other commercially available proteases include Neutrase™, Ronozyme™ Pro, Maxatase™, Maxacal™, Maxapem™, Opticlean™, Properase™, Purafast™, Purafect™, Purafect Ox™, Purafact Prime™, Excellase™, FN2™, FN3™ and FN4™ (available from Novozymes, Genencor International Inc., Gist-Brocades, BASF, or DSM). Other examples are Primase™ and Duralase™. Blap R, Blap S and Blap X available from Henkel are also examples.

Lyases:

The lyase may be a pectate lyase derived from *Bacillus*, particularly *B. licherniformis* or *B. agaradhaerens*, or a variant derived of any of these, e.g. as described in U.S. Pat. No. 6,124,127, WO 99/027083, WO 99/027084, WO 02/006442, WO 02/092741, WO 03/095638, Commercially available pectate lyases are XPect; Pectawash and Pectaway (Novozymes A/S).

Mannanase:

The mannanase may be an alkaline mannanase of Family 5 or 26. It may be a wild-type from *Bacillus* or *Humicola*, particularly *B. agaradhaerens, B. licheniformis, B. halodurans, B. clausii,* or *H. insolens*. Suitable mannanases are described in WO 99/064619. A commercially available mannanase is Mannaway (Novozymes A/S).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium,* e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Lipases and Cutinases:

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g., *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO 2007/087508 and WO 2009/109500.

Preferred commercially available lipase enzymes include Lipolase™, Lipolase Ultra™' and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp. lipase from Solvay.

In an embodiment of the invention, the amino acid sequence of the lipase has at least 70% sequence identity, preferably at least 75%, more preferably at least 80%, more preferably at least 85%, more preferably at least 90%, more preferably at least 95%, 96%, 97%, 98%, 99%, and most preferably 100% sequence identity to the amino acid sequence of SEQ ID NO: 1. In another embodiment, the number of amino acid substitutions, deletions and/or insertions introduced into the amino acid sequence of SEQ ID NO: 1 is up to 10, e.g., 1, 2, 3, 4, 5, 6, 7, 8, 9, or 10; or up to 5, e.g., 1, 2, 3, 4, or 5.

Amylases:

Suitable amylases ($\alpha$ and/or $\beta$) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Stainzyme; Stainzyme Plus; Duramyl™' Termamyl™, Termamyl Ultra; Natalase, Fungamyl™ and BAN™ (Novozymes A/S), Rapidase™ and Purastar™/Effectenz™, Powerase and Preferenz S100 (from Genencor International Inc./DuPont).

Deoxyribonuclease (DNase):
Suitable deoxyribonucleases (DNases) are any enzyme that catalyzes the hydrolytic cleavage of phosphodiester linkages in the DNA backbone, thus degrading DNA. According to the invention, a DNase which is obtainable from a bacterium is preferred; in particular a DNase which is obtainable from a *Bacillus* is preferred; in particular a DNase which is obtainable from *Bacillus subtilis* or *Bacillus licheniformis* is preferred. Examples of such DNases are described in patent application WO 2011/098579 or in PCT/EP2013/075922.

Perhydrolases:
Suitable perhydrolases are capable of catalyzing a perhydrolysis reaction that results in the production of a peracid from a carboxylic acid ester (acyl) substrate in the presence of a source of peroxygen (e.g., hydrogen peroxide). While many enzymes perform this reaction at low levels, perhydrolases exhibit a high perhydrolysis:hydrolysis ratio, often greater than 1. Suitable perhydrolases may be of plant, bacterial or fungal origin. Chemically modified or protein engineered mutants are included.

Examples of useful perhydrolases include naturally occurring *Mycobacterium* perhydrolase enzymes, or variants thereof. An exemplary enzyme is derived from *Mycobacterium smegmatis*. Such enzyme, its enzymatic properties, its structure, and variants thereof, are described in WO 2005/056782, WO 2008/063400, US 2008/145353, and US2007167344.

Oxidases/Peroxidases:

Suitable oxidases and peroxidases (or oxidoreductases) include various sugar oxidases, laccases, peroxidases and haloperoxidases.

Suitable peroxidases include those comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase for use in the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Examples of other oxidases include, but are not limited to, amino acid oxidase, glucose oxidase, lactate oxidase, galactose oxidase, polyol oxidase (e.g., WO2008/051491), and aldose oxidase. Oxidases and their corresponding substrates may be used as hydrogen peroxide generating enzyme systems, and thus a source of hydrogen peroxide. Several enzymes, such as peroxidases, haloperoxidases and perhydrolases, require a source of hydrogen peroxide. By studying EC 1.1.3._, EC 1.2.3._, EC 1.4.3._, and EC 1.5.3._ or similar classes (under the International Union of Biochemistry), other examples of such combinations of oxidases and substrates are easily recognized by one skilled in the art.

Amino acid changes in the lipase amino acid sequence shown as SEQ ID NO: 1, as referenced above, may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for enzyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

The relatedness between two amino acid sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment).

Enzyme Stabilizers and/or Rheology Modifiers

The microcapsules may also contain enzyme stabilizers as known in the art, e.g., polyols, polymers, reversible enzyme inhibitors, divalent cations, enzyme substrates, antioxidants etc. Water soluble stabilizers are preferred.

Addition of slowly dissolving stabilizers can be used to create a local environment inside the capsule, which is more "friendly" to the encapsulated enzyme/compound, thus improving the stability during storage.

Examples of reversible protease inhibitors are boronic acids, peptide aldehydes and derivatives hereof and high molecular protein-type inhibitors (like BASI/RASI inhibitors, see WO 2009/095425). An example of metalloprotease inhibitors is described in WO 2008/134343. Protease inhibitors are described in more detail below under the heading "Protease Inhibitors".

Stabilizing polymers can be based on, e.g., polyvinylypyrrolidon, polyvinylacetate, polyvinylalcohol and copolymers hereof. Stabilizing polyols can be smaller molecules like glycerol, sorbitol, propylene glycol etc. but also larger molecules like polyethylene glycol, polysaccharides etc.

Of stabilizing divalent cations $Ca^{2+}$, $Mg^{2+}$ and $Zn^{2+}$ are well-known in the art. Thus, in an embodiment, the microcapsules of the invention comprise a source of $Ca^{2+}$, $Mg^{2+}$ or $Zn^{2+}$ ions. Preferably, the source of $Ca^{2+}$, $Mg^{2+}$ or $Zn^{2+}$ ions is a poorly soluble (slowly dissolving) salt of $Ca^{2+}$, $Mg^{2+}$ or $Zn^{2+}$. Poorly soluble means that the solubility in pure water at 20° C. is less than 5 g/l, 2 g/l, 1 g/l, 0.5 g/l, 0.2 g/l, 0.1 g/l, or 0.05 g/l. Preferred salts of $Ca^{2+}$, $Mg^{2+}$ or $Zn^{2+}$ are calcium carbonate, magnesium carbonate, zinc carbonate, calcium sulfate, calcium sulfite, magnesium sulfite, zinc sulfite, calcium phosphate, dicalcium phosphate, magnesium phosphate, zinc phosphate, calcium citrate, magnesium citrate, zinc citrate, calcium oxalate, magnesium oxalate, zinc oxalate, calcium tartrate, magnesium tartrate, or zinc tartrate.

Also slowly dissolving acids or bases can be used to create a local pH inside the microcapsule, which is more "friendly" to the encapsulated enzyme/compound.

Enzymes are in most cases stabilized by addition of their substrates (e.g., protein for proteases, starch for amylases etc.). Antioxidants or reducing agents can be applied to reduce oxidation of enzymes, e.g., thiosulfate, ascorbate etc. The net dosage needed of these stabilizers per gram detergent is much lower compared to adding the stabilizers to the continuous detergent phase, as they are concentrated in the internal capsule phase, and will in many cases either not diffuse out during storage, or only slowly diffuse out depending on the structure and molecular weight of the stabilizer. Especially high molecular weight stabilizers (e.g., higher than 1 kDa, or higher than 2 kDa more preferred higher than 5 kDa) will give improved net efficiency. High molecular weight inhibitors, polymers, polyols, cations, enzyme substrates and antioxidants are thus preferred.

The enzyme may be protected by addition of a "scavenger" protein. Components destabilizing enzyme by reacting onto amino acid groups (e.g., amines) on the protein may thus react with the scavenger or sacrificial protein added. Scavenger protein with a sufficient large molecular weight to stay inside the capsules are preferred.

A somewhat different way to improve the enzyme stability is to add rheology modifying components that increase viscosity of the internal capsule phase. An increased internal viscosity will slow down diffusion of enzyme destabilizers into the capsules (and/or slow down the diffusion of enzyme stabilizers out of the capsule) and thus prolong the lifetime of the enzyme. Examples of such viscosity modifiers are polymers like polyethylene glycol (PEG), polyethylene oxide (PEO), hydrophilic polyurethane, polyvinylpyrrolidon (PVP) and PVP vinyl acetate copolymers, starch, hyaluronic acid, water soluble cellulose derivatives like carboxymethyl cellulose, water soluble gums like gum Arabic, locust bean gum, guar gum or xanthan gum etc. and combinations or copolymers hereof. Most preferred are nonionic high molecular weight polymers, with a molecular weight higher than 1 kDa, or higher than 2 kDa, more preferred higher than 5 kDa. Nonionic polymers are preferred as they in most cases are more compatible with the reactive membrane polymer than ionic polymers.

The high viscosity can either be accomplished by producing the capsules using a high viscosity aqueous phase, or—more sophisticated—producing capsules where the viscosity increase first occur after producing the emulsion/capsules. This "triggered" viscosity increase is preferable as preparing emulsions with a high viscosity aqueous phase can be difficult. Triggered viscosity increase can be done in situ when added to detergent by the internal capsule phase having a higher water activity than the detergent to which it is added, thus water will diffuse out of the capsules (but not the rheology modifier) increasing the viscosity of the internal phase after addition to detergent. This can also be utilized using diffusion of salt or other low molecular components, e.g., by having a component that will increase viscosity when salt concentration is reduced by addition to detergent (e.g., a polymer that is precipitated at the initial high salt content but soluble when salt concentration is reduced due to diffusion of salt when added to detergent). Another way to trigger viscosity is to use components where the viscosity is dependent on the pH. For some interfacial polymerization processes (e.g., amine—acid halogen reaction) the pH of the internal phase will change during encapsulation, in the case of amine-acid halogen pH will be reduced during the interfacial polymerization. This can be used to trigger an increase in viscosity. Many rheology modifiers like polyacrylates show a viscosity maximum at a specific pH or pH range. Carbopol 934 from Lubrizol and Texipol 63-258 from Scott-Bader are examples of rheology modifiers where viscosity is significantly increased when reducing the pH from 11 to 8, or increasing pH from 4 to 8. Another polymer type with a different viscosity at low pH and at high pH is partially hydrolyzed polyacrylamide. Yet another possibility is to use rheology modifiers which are temperature dependent, thus making the emulsion/encapsulation at one temperature, and subsequently changing the temperature to increase viscosity. Also a light or ultrasound induced viscosity can be utilized. Yet another method is to use shear-thinning rheology modifiers, such that the viscosity is low at high shear when the emulsion is formed and high when shear is reduced.

Another stabilization technique is to assure that the enzyme is precipitated in the capsules during storage, for example by addition of precipitants like salt or polyethylene glycol (PEG). The same "triggered stabilization" as described above can be used, e.g., by addition of PEG, which after addition to detergent is concentrated by water diffusing out to a degree where the enzyme will precipitate. In this way the enzyme can be in solution during processing of the capsules, but precipitated when added to detergent.

Enzymes can also be used in precipitated or crystal form when preparing the microcapsules.

Liquid Detergent Composition

The microcapsules of the invention may be added to, and thus form part of, any detergent composition in any form, such as liquid and powder detergents, and soap and detergent bars (e.g., syndet bars).

In one embodiment, the invention is directed to liquid detergent compositions comprising a microcapsule, as described above, in combination with one or more additional cleaning composition components.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be either isotropic or structured, preferably isotropic. It may be a formulation useful for washing in automatic washing machines or for hand washing, or for (automatic) dish wash. It may also be a personal care product, such as a shampoo, toothpaste, or a hand soap.

The liquid detergent composition may be aqueous, typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry and dish wash. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s)

is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0.1% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0.1% to about 20% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0.1% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see for example review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg ions. Any builder and/or co-builder known in the art for use in laundry detergents may be utilized. Non-limiting examples of builders include citrates, zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-50% by weight, such as about 5% to about 30%, of a detergent co-builder, or a mixture thereof. The detergent composition may include a co-builder alone, or in combination with a builder, for example a citrate builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N, N'-triacetate (HEDTA), diethanolglycine (DEG), diethylenetriamine penta (methylenephosphonic acid) (DTPMP), aminotris (methylenephosphonic acid) (ATMP), and combinations and salts thereof. Further exemplary builders and/or co-builders are described in, e.g., WO 09/102854, U.S. Pat. No. 5,977,053.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575 and U.S. Pat. No. 5,955,415. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

(Additional) Enzymes

Enzyme(s) which may be comprised in the detergent composition, which are not contained in a microcapsule, include one or more enzymes such as a protease, lipase, cutinase, amylase, carbohydrase, cellulase, pectinase, mannanase, arabinase, galactanase, xanthanase, xylanase, DNAse, perhydrolase, and/or oxidoreductases (e.g., laccase, peroxidase, peroxygenase and/or haloperoxidase).

Such enzyme(s) may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708. Other stabilizers and inhibitors as known in the art can be added (see below). Examples of such enzymes are the same as those, which can be encapsulated in the microcapsule, as shown above.

When the microcapsule of the invention is used to encapsulate one or more enzymes detrimental to the stability of detergent components (e.g., xanthan gum, polymers with ester bonds, hydrogenated castor oil, perfume, methyl ester sulfonate surfactants, cellulose, cellulose derivatives, dextrin, and cyclodextrin), it may be useful to add components to the liquid detergent which inactivates any leaked enzyme(s) from the microcapsules. This can be done, e.g., by adding a protease to the detergent composition. If the microcapsules leak small amounts of the encapsulated enzymes, the protease can then be used as a scavenger to degrade the enzyme leaked from the microcapsules, and thus avoid degradation of sensitive detergent components.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a liquid, slurry, or even a granulate, etc.

Protease Inhibitors

The detergent composition may include a protease inhibitor, which is a reversible inhibitor of protease activity, e.g., serine protease activity. Preferably, the protease inhibitor is a (reversible) subtilisin protease inhibitor. In particular, the protease inhibitor may be a peptide aldehyde, boric acid, or a boronic acid; or a derivative of any of these.

The protease inhibitor may have an inhibition constant to a serine protease, $K_i$ (mol/L) of from 1E-12 to 1E-03; more preferred from 1E-11 to 1E-04; even more preferred from 1E-10 to 1E-05; even more preferred from 1E-10 to 1E-06; and most preferred from 1E-09 to 1E-07.

The protease inhibitor may be boronic acid or a derivative thereof; preferably, phenylboronic acid or a derivative thereof.

In an embodiment of the invention, the phenyl boronic acid derivative is of the following formula:

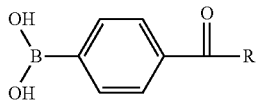

wherein R is selected from the group consisting of hydrogen, hydroxy, $C_1$-$C_6$ alkyl, substituted $C_1$-$C_6$ alkyl, $C_1$-$C_6$ alkenyl and substituted $C_1$-$C_6$ alkenyl. Preferably, R is hydrogen, $CH_3$, $CH_3CH_2$ or $CH_3CH_2CH_2$.

In a preferred embodiment, the protease inhibitor (phenyl boronic acid derivative) is 4-formyl-phenyl-boronic acid (4-FPBA).

In another particular embodiment, the protease inhibitor is selected from the group consisting of:
thiophene-2 boronic acid, thiophene-3 boronic acid, acetamidophenyl boronic acid, benzofuran-2 boronic acid, naphtalene-1 boronic acid, naphtalene-2 boronic acid, 2-FPBA, 3-FBPA, 4-FPBA, 1-thianthrene boronic acid, 4-dibenzofuran boronic acid, 5-methylthiophene-2 boronic, acid, thionaphtrene boronic acid, furan-2 boronic acid, furan-3 boronic acid, 4,4 biphenyl-diborinic acid, 6-hydroxy-2-naphtalene, 4-(methylthio) phenyl boronic acid, 4 (trimethyl-silyl)phenyl boronic acid, 3-bromothiophene boronic acid, 4-methylthiophene boronic acid, 2-naphtyl boronic acid, 5-bromothiphene boronic acid, 5-chlorothiophene boronic acid, dimethylthiophene boronic acid, 2-bromophenyl boronic acid, 3-chlorophenyl boronic acid, 3-methoxy-2-thiophene, p-methyl-phenylethyl boronic acid, 2-thianthrene boronic acid, di-benzothiophene boronic acid, 4-carboxyphenyl boronic acid, 9-anthryl boronic acid, 3,5 dichlorophenyl boronic, acid, diphenyl boronic acidanhydride, o-chlorophenyl boronic acid, p-chlorophenyl boronic acid, m-bromophenyl boronic acid, p-bromophenyl boronic acid, p-flourophenyl boronic acid, p-tolyl boronic acid, o-tolyl boronic acid, octyl boronic acid, 1,3,5 trimethylphenyl boronic acid, 3-chloro-4-flourophenyl boronic acid, 3-aminophenyl boronic acid, 3,5-bis-(triflouromethyl) phenyl boronic acid, 2,4 dichlorophenyl boronic acid, 4-methoxyphenyl boronic acid.

Further boronic acid derivatives suitable as protease inhibitors in the detergent composition are described in U.S. Pat. Nos. 4,963,655, 5,159,060, WO 95/12655, WO 95/29223, WO 92/19707, WO 94/04653, WO 94/04654, U.S. Pat. Nos. 5,442,100, 5,488,157 and 5,472,628.

The protease inhibitor may also be a peptide aldehyde having the formula $X$—$B^1$—$B^0$—H, wherein the groups have the following meaning:
a) H is hydrogen;
b) $B^0$ is a single amino acid residue with L- or D-configuration and with the formula: NH—CHR'—CO;
c) $B^1$ is a single amino acid residue; and
d) X consists of one or more amino acid residues (preferably one or two), optionally comprising an N-terminal protection group.

NH—CHR'—CO($B^0$) is an L or D-amino acid residue, where R' may be an aliphatic or aromatic side chain, e.g., aralkyl, such as benzyl, where R' may be optionally substituted. More particularly, the $B^0$ residue may be bulky, neutral, polar, hydrophobic and/or aromatic. Examples are the D- or L-form of Tyr (p-tyrosine), m-tyrosine, 3,4-dihydroxyphenylalanine, Phe, Val, Met, norvaline (Nva), Leu, Ile or norleucine (Nle).

In the above formula, X—$B^1$—$B^0$—H, the $B^1$ residue may particularly be small, aliphatic, hydrophobic and/or neutral. Examples are alanine (Ala), cysteine (Cys), glycine (Gly), proline (Pro), serine (Ser), threonine (Thr), valine (Val), norvaline (Nva) and norleucine (Nle), particularly alanine, glycine, or valine.

X may in particular be one or two amino acid residues with an optional N-terminal protection group (i.e. the compound is a tri- or tetrapeptide aldehyde with or without a protection group). Thus, X may be $B^2$, $B^3$—$B^2$, Z—$B^2$, or Z—$B^3$—$B^2$ where $B^3$ and $B^2$ each represents one amino acid residue, and Z is an N-terminal protection group. The $B^2$ residue may in particular be small, aliphatic and/or neutral, e.g., Ala, Gly, Thr, Arg, Leu, Phe or Val. The $B^3$ residue may in particular be bulky, hydrophobic, neutral and/or aromatic, e.g., Phe, Tyr, Trp, Phenylglycine, Leu, Val, Nva, Nle or Ile.

The N-terminal protection group Z (if present) may be selected from formyl, acetyl, benzoyl, trifluoroacetyl, fluoromethoxy carbonyl, methoxysuccinyl, aromatic and aliphatic urethane protecting groups, benzyloxycarbonyl (Cbz), t-butyloxycarbonyl, adamantyloxycarbonyl, p-methoxybenzyl carbonyl (MOZ), benzyl (Bn), p-methoxybenzyl (PMB) or p-methoxyphenyl (PMP), methoxycarbonyl (Moc); methoxyacetyl (Mac); methyl carbamate or a methylamino carbonyl/methyl urea group. In the case of a tripeptide aldehyde with a protection group (i.e. X=Z—$B^2$), Z is preferably a small aliphatic group, e.g., formyl, acetyl, fluoromethoxy carbonyl, t-butyloxycarbonyl, methoxycarbonyl (Moc); methoxyacetyl (Mac); methyl carbamate or a Methylamino carbonyl/methyl urea group. In the case of a tripeptide aldehyde with a protection group (i.e. X=Z—$B^3$—$B^2$), Z is preferably a bulky aromatic group such as benzoyl, benzyloxycarbonyl, p-methoxybenzyl carbonyl (MOZ), benzyl (Bn), p-methoxybenzyl (PMB) or p-methoxyphenyl (PMP).

Suitable peptide aldehydes are described in WO 94/04651, WO 95/25791, WO 98/13458, WO 98/13459, WO 98/13460, WO 98/13461, WO 98/13461, WO 98/13462, WO 2007/141736, 2007/145963, WO 2009/118375, WO 2010/055052 and WO 2011/036153. More particularly, the peptide aldehyde may be Cbz-RAY-H, Ac-GAY-H, Cbz-GAY-H, Cbz-GAL-H, Cbz-VAL-H, Cbz-GAF-H, Cbz-GAV-H, Cbz-GGY-H, Cbz-GGF-H, Cbz-RVY-H, Cbz-LVY-H, Ac-LGAY-H, Ac-FGAY-H, Ac-YGAY-H, Ac-FGAL-H, Ac-FGAF-H, Ac-FGVY-H, Ac-FGAM-H, Ac-WLVY-H, MeO—CO-VAL-H, MeNCO-VAL-H, MeO—CO-FGAL-H, MeO—CO-FGAF-H, $MeSO_2$-FGAL-H, $MeSO_2$-VAL-H, $PhCH_2O(OH)(O)P$-VAL-H, $EtSO_2$-FGAL-H, $PhCH_2SO_2$-VAL-H, $PhCH_2O(OH)(O)P$-LAL-H, $PhCH_2O(OH)(O)P$-FAL-H, or $MeO(OH)(O)P$-LGAL-H. Here, Cbz is benzyloxycarbonyl, Me is methyl, Et is ethyl, Ac is acetyl, H is hydrogen, and the other letters represent amino acid residues denoted by standard single letter notification (e.g., F=Phe, Y=Tyr, L=Leu).

Alternatively, the peptide aldehyde may have the formula as described in WO 2011/036153:

$$P-O-(A-X')_n-A_{n+1}-Q$$

wherein Q is hydrogen, $CH_3$, $CX''_3$, $CHX''_2$, or $CH_2X''$, wherein X" is a halogen atom;

wherein one X' is the "double N-capping group" CO, CO—CO, CS, CS—CS or CS—CO, most preferred urido (CO), and the other X' are nothing, wherein n=1-10, preferably 2-5, most preferably 2, wherein each of $A_i$ and $A_{n+1}$ is an amino acid residue having the structure:

—NH—CR"—CO— for a residue to the right of X'=CO—, or

—CO—CR"—NH— for a residue to the left of X'=CO— wherein R" is H— or an optionally substituted alkyl or alkylaryl group which may optionally include a hetero atom and may optionally be linked to the N atom, and wherein P is hydrogen or any C-terminal protection group.

Examples of such peptide aldehydes include α-MAPI, β-MAPI, F-urea-RVY-H, F-urea-GGY-H, F-urea-GAF-H, F-urea-GAY-H, F-urea-GAL-H, F-urea-GA-Nva-H, F-urea-GA-Nle-H, Y-urea-RVY-H, Y-urea-GAY-H, F—CS-RVF-H, F—CS-RVY-H, F—CS-GAY-H, Antipain, GE20372A, GE20372B, Chymostatin A, Chymostatin B, and Chymostatin C. Further examples of peptide aldehydes are disclosed in WO 2010/055052 and WO 2009/118375, WO 94/04651, WO 98/13459, WO 98/13461, WO 98/13462, WO 2007/145963, hereby incorporated by reference.

Alternatively to a peptide aldehyde, the protease inhibitor may be a hydrosulfite adduct having the formula X—$B^1$—NH—CHR—CHOH—$SO_3$M, wherein X, $B^1$ and R are defined as above, and M is H or an alkali metal, preferably Na or K.

The peptide aldehyde may be converted into a water-soluble hydrosulfite adduct by reaction with sodium bisulfite, as described in textbooks, e.g., March, J. Advanced Organic Chemistry, fourth edition, Wiley-Interscience, US 1992, p 895.

An aqueous solution of the bisulfite adduct may be prepared by reacting the corresponding peptide aldehyde with an aqueous solution of sodium bisulfite (sodium hydrogen sulfite, $NaHSO_3$); potassium bisulfite ($KHSO_3$) by known methods, e.g., as described in WO 98/47523; U.S. Pat. Nos. 6,500,802; 5,436,229; *J. Am. Chem. Soc.* (1978) 100, 1228; *Org. Synth., Coll.* vol. 7: 361.

The molar ratio of the above-mentioned peptide aldehydes (or hydrosulfite adducts) to the protease may be at least 1:1 or 1.5:1, and it may be less than 1000:1, more preferred less than 500:1, even more preferred from 100:1 to 2:1 or from 20:1 to 2:1, or most preferred, the molar ratio is from 10:1 to 2:1.

Formate salts (e.g., sodium formate) and formic acid have also shown good effects as inhibitor of protease activity. Formate can be used synergistically with the above-mentioned protease inhibitors, as shown in WO 2013/004635. The formate salts may be present in the detergent composition in an amount of at least 0.1% w/w or 0.5% w/w, e.g., at least 1.0%, at least 1.2% or at least 1.5%. The amount of the salt is typically below 5% w/w, below 4% or below 3%.

In an embodiment, the protease is a metalloprotease and the inhibitor is a metalloprotease inhibitor, e.g., a protein hydrolysate based inhibitor (e.g., as described in WO 2008/134343).

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent—

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers—

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers are structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of the composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Bleaching Systems

Due to the incompatibility of the components there are still only few examples of liquid detergents combining bleach and enzymes (e.g., U.S. Pat. No. 5,275,753 or WO 99/00478). The enzyme microcapsules described in this invention can be used to physically separate bleach from enzyme in liquid detergents. The detergent may contain 0-50% of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetraacetylethylene diamine (TAED), sodium 4-[(3,5,5-trimethylhexanoyl)oxy] benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

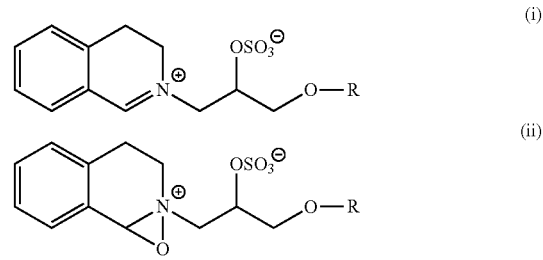

and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Formulation of Detergent Products

The liquid detergent composition of the invention may be in any convenient form, e.g., a pouch having one or more compartments, a gel, or a regular, compact or concentrated liquid detergent (see e.g., WO 2009/098660 or WO 2010/141301).

Pouches can be configured as single or multi compartments. It can be of any form, shape and material which is suitable for holding the composition, e.g., without allowing release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids.

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

Compositions, Methods and Uses

In a first aspect, the present invention provides a microcapsule composition, comprising a compound, such as an enzyme, entrapped in a compartment formed by a membrane, which membrane is produced by cross-linking of (a) a polybranched polyamine having a molecular weight of more than 800 Da, and (b) an aliphatic or aromatic amine having a molecular weight of less than 300 Da; wherein the weight ratio of (a)/(b) is in the range of 0.1 to 1000.

In an embodiment, the compound is a detergent component. Preferably, the detergent component is reactive (such as an enzyme substrate or co-substrate) or incompatible with other detergent components.

In an embodiment, the compound is an enzyme selected from the group consisting of protease, metalloprotease, subtilisin, amylase, lipase, cutinase, cellulase, mannanase, pectinase, xanthanase, DNAse, laccase, peroxidase, haloperoxidase, perhydrolase, and combinations thereof; preferably the enzyme is a lipase.

Examples of enzyme substrates or co-substrates include, but are not limited to, hydrogen peroxide or hydrogen peroxide precursors like percarbonates or perborates (substrates of oxidoreductases like peroxidase/haloperoxidase), sugars or polyols for in situ hydrogen peroxide generation (substrates of oxidases), ester substrates like propylene glycol diacetate (substrates of perhydrolase), and laccase/peroxidase mediators.

In an embodiment, the reactive amino groups of the polybranched polyamine constitute at least 15% of the molecular weight.

In an embodiment, the diameter of the compartment formed by the membrane of the microcapsule is at least 50 micrometers.

In an embodiment, the compartment contains at least 1% active enzyme by weight of the total compartment.

In an embodiment, the microcapsule composition further includes an alcohol, such as a polyol.

In an embodiment, the molecular weight of the polybranched polyamine, (a), is at least 1 kDa.

In an embodiment, the polybranched polyamine, (a), is a polyethyleneimine.

In an embodiment, the molecular weight of the aliphatic or aromatic amine, (b), is less than 250 Da.

In an embodiment, the weight ratio of the polybranched polyamine, (a), and the aliphatic or aromatic amine, (b): (polybranched polyamine)/(aliphatic or aromatic amine) is in the range of 0.1 to 500; preferably in the range of 0.1 to 250; more preferably in the range of 1 to 250.

In an embodiment, the aliphatic or aromatic amine, (b), is an aliphatic amine; preferably (b) is an alkylamine with one or more amino groups; more preferably (b) is an ethyleneamine or alkanolamine; and most preferably (b) is selected from the group consisting of ethylene diamine, diethylene triamine, triethylene tetraamine, bis(3-aminopropyl)amine, hexamethylene diamine, monoethanolamine, diethanolamine, and triethanolamine.

In an embodiment, the compartment formed by the membrane of the microcapsule comprises a source of $Mg^{2+}$, $Ca^{2+}$, or $Zn^{2+}$ ions, such as a poorly soluble salt of $Mg^{2+}$, $Ca^{2+}$, or $Zn^{2+}$.

In an embodiment, the membrane of the microcapsule is produced by using an acid chloride as crosslinking agent; preferably adipoyl chloride, sebacoyl chloride, dodecanedioc acid chloride, phthaloyl chloride, terephthaloyl chloride, isophthaloyl chloride, or trimesoyl chloride; and more preferably isophtaloyl chloride, terephthaloyl chloride, or trimesoyl chloride.

In an embodiment, the membrane is produced by interfacial polymerization.

In an embodiment, the microcapsule composition is capable of releasing at least 50% of the entrapped/encapsulated compound (such as an enzyme) within 5 minutes, after storage in a concentrated liquid detergent overnight, and subsequently diluted 1:1000 in pure water.

In a second aspect, the present invention provides a liquid detergent composition, comprising a surfactant and/or a detergent builder, and the microcapsule composition as described above, including all embodiments. Preferably, the surfactant is an anionic surfactant.

In an embodiment, the liquid detergent composition comprises at least two mutually incompatible or reactive components, wherein one of the components is entrapped in (located inside) the compartment of the microcapsule, and the other component is not entrapped in (located outside) the compartment of the microcapsule.

In other aspects, the invention also provides for use of the compositions of the invention, as described above, for laundry wash or automatic dish wash. The compositions may also be used for improving the stability of the compound encapsulated (entrapped) in the microcapsule (compartment). In particular, the invention provides for use of the compositions for improving storage stability of an encapsulated enzyme.

The invention also provides a method for preparing the microcapsule composition of the invention, comprising entrapping a compound, such as an enzyme in a compartment formed by a membrane, which membrane is produced by cross-linking of (a) a polybranched polyamine having a molecular weight of more than 800 Da, and (b) an aliphatic or aromatic amine having a molecular weight of less than 300 Da; wherein the weight ratio of (a)/(b) is in the range of 0.1 to 1000.

Embodiments of the method and use, according to the invention, are the same as the embodiments of the compositions of the invention, as described above.

The microcapsules of the invention can be used in detergent compositions of high or low reserve alkalinity (see WO 2006/090335). The microcapsules are also compatible with compositions of high or low levels of zeolite, phosphate, or other strong or weak builders (chelators, sequestrants, precipitants) used for interacting with calcium and magnesium ions.

The use in laundry wash or automatic dish wash, according to the invention, may be carried out at a temperature from 5 to 90 degrees Celsius, preferably from 5 to 70 degrees Celsius, more preferably from 5 to 60 degrees Celsius, even more preferably from 5 to 50 degrees Celsius, even more preferably from 5 to 40 degrees Celsius, most preferably from 5 to 30 degrees Celsius, and in particular from 10 to 30 degrees Celsius.

The present invention is further described by the following examples which should not be construed as limiting the scope of the invention.

EXAMPLES

Chemicals used as buffers and substrates were commercial products of at least reagent grade. Lipase1 has the amino acid sequence shown in SEQ ID NO: 1 (also described in International patent application no. PCT/EP2014/059701).

A commercially available enzyme-free liquid detergent, "Persil Small and Mighty Non-biological", was purchased in the United Kingdom in June 2014. This detergent is referred to as "Detergent B".

Example 1

Improved Enzyme Stability by Addition of Small Aliphatic Amines

Aqueous phase solutions I to VII were prepared by mixing an aqueous solution of Lipase1 (120 mg active enzyme per gram) with a polybranched polyamine from Table 1 and a small aliphatic amine from Table 2, according to the experimental setup shown in Table 3.

TABLE 1

Properties of some small aliphatic amines (alkanolamines and ethyleneamines).

| Small amine | Abbreviations | CAS no. | Mw |
|---|---|---|---|
| Monoethanolamine | MEA | 141-43-5 | 61.08 |
| Diethanolamine | DEA | 111-42-2 | 105.14 |

TABLE 1-continued

Properties of some small aliphatic amines (alkanolamines and ethyleneamines).

| Small amine | Abbreviations | CAS no. | Mw |
|---|---|---|---|
| Ethylene diamine | EDA | 107-15-3 | 116.90 |
| Diethylene triamine | DETA | 111-40-0 | 206.70 |
| Linear triethylene tetramine | L-TETA | 112-24-3 | 146.23 |
| Bis(3-aminopropyl)amine | DPTA | 56-18-8 | 131.22 |
| Hexamethylene diamine | HMDA | 124-09-4 | 116.24 |

TABLE 2

Properties of some polybranched polyamines.

| Polybranched polyamine | Molecular weight (kDa) | Ratio of primary/secondary/tertiary amines |
|---|---|---|
| Lupasol G20 | 1.3 | 39%/36%/25% |
| Lupasol G100 | 5.0 | 36%/37%/27% |
| Epomin SP-012 | 1.2 | 25%/50%/25% |
| Epomin SP-200 | 10.0 | 35%/35%/30% |

TABLE 3

Experimental setup.

| Components in aqueous phase | I (g) | II (g) | III (g) | IV (g) | V (g) | VI (g) | VII (g) |
|---|---|---|---|---|---|---|---|
| Lipase1 solution, 120 mg/g | 25 | 25 | 25 | 25 | 25 | 25 | 25 |
| Lupasol G100 (50% in water) | 8 | 8 | 0 | 0 | 0 | 0 | 0 |
| Epomin SP-012 (99+% in water) | 0 | 0 | 3 | 3 | 3 | 3 | 0 |
| Epomin SP-200 (99+% in water) | 0 | 0 | 0 | 0 | 0 | 0 | 3 |
| DETA | 0 | 0.5 | 0 | 0.5 | 0 | 0 | 0.5 |
| MEA | 0 | 0 | 0 | 0 | 0.5 | 0 | 0 |
| L-TETA | 0 | 0 | 0 | 0 | 0 | 0.5 | 0 |
| Water | Ad 50 g | | | | | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 μm and 150 μm.

A reactant oil phase was prepared by dissolving 49 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from ExxonMobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 40° C. for 2 week (accelerated conditions).

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 4. The stability improvements were calculated relative to the non-encapsulated reference.

TABLE 4

Residual activity of the encapsulated lipase after storage.

| Components | Residual activity (2 weeks at 40° C.) | Stability improvement |
|---|---|---|
| I: Lupasol G100 | 2% | 4 |
| II: Lupasol G100 + DETA | 55% | 110 |
| III: Epomin SP-012 | 5% | 10 |
| IV: Epomin SP-012 + DETA | 54% | 108 |
| V: Epomin SP-012 + MEA | 9% | 18 |
| VI: Epomin SP-012 + L-TETA | 62% | 124 |
| VII: Epomin SP-200 + DETA | 56% | 112 |
| Non-encapsulated reference | 0.5% | 1 |

The results demonstrate that small amines can be added to different polymers and improve the enzymatic stability in laundry detergent Example 2

Improved Enzyme Stability by Addition of a Small Amine in Different Concentrations Aqueous phase solutions I to VI were prepared by mixing an aqueous solution of Lipase1 (120 mg active enzyme per gram) with a polybranched polyamine from Table 1 and a small amine from Table 2, according to the experimental setup shown in Table 5.

TABLE 5

Experimental setup.

| Components in aqueous phase | I (g) | II (g) | III (g) | IV (g) | V (g) | VI (g) |
|---|---|---|---|---|---|---|
| Lipase1 solution, 120 mg/g | 25 | 25 | 25 | 25 | 25 | 25 |
| Lupasol G100 (50% in water) | 4 | 4 | 4 | 4 | 4 | 4 |
| DETA | 0 | 0.015 | 0.25 | 0.5 | 0.75 | 1.5 |
| Water | Ad 50 g | | | | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 µm and 150 µm.

A reactant oil phase was prepared by dissolving 49 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from ExxonMobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 40° C. for 2 week (accelerated conditions).

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 6. The stability improvements were calculated relative to the non-encapsulated reference.

TABLE 6

Residual activity of the encapsulated lipase after storage.

| Components | Weight ratio of Lupasol G100/DETA | Residual activity (2 weeks, 40° C.) | Stability improvement |
|---|---|---|---|
| I: Lupasol G100 | — | 2% | 4 |
| II: Lupasol G100 + 0.03% DETA | 133.3 | 27% | 54 |
| III: Lupasol G100 + 0.5% DETA | 8 | 54% | 108 |
| IV: Lupasol G100 + 1% DETA | 4 | 52% | 104 |
| V: Lupasol G100 + 1.5% DETA | 2.7 | 55% | 110 |
| VI: Lupasol G100 + 3% DETA | 1.3 | 54% | 108 |
| Non-encapsulated reference | — | 0.5% | 1.0 |

The results demonstrate that even small amounts of a small amine, added to the aqueous phase when preparing the microcapsule, improves the stability of an encapsulated enzyme in a detergent composition.

Example 3

Improved Enzyme Stability by Addition of Different Small Amine

Aqueous phase solutions I to VI were prepared by mixing an aqueous solution of Lipase1 (120 mg active enzyme per gram) with a polybranched polyamine from Table 1 and a small amine from Table 2, according to the experimental setup shown in Table 7.

TABLE 7

Experimental setup.

| Components in aqueous phase | I (g) | II (g) | III (g) | IV (g) | V (g) | VI (g) |
|---|---|---|---|---|---|---|
| Lipase1 solution, 120 mg/g | 41 | 41 | 41 | 41 | 41 | 41 |
| Lupasol G100 (50% in water) | 8 | 8 | 8 | 8 | 8 | 8 |
| DETA | 0 | 0.5 | 0 | 0 | 0 | 0 |
| MEA | 0 | 0 | 0.5 | 0 | 0 | 0 |
| DEA | 0 | 0 | 0 | 0.5 | 0 | 0 |
| L-TETA | 0 | 0 | 0 | 0 | 0.5 | 0 |
| DPTA | 0 | 0 | 0 | 0 | 0 | 0.5 |
| Water | Ad 50 g | | | | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 µm and 150 µm.

A reactant oil phase was prepared by dissolving 28 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from Exxon Mobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 37° C. for 2 week (accelerated conditions).

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 8. The stability improvements were calculated relative to the non-encapsulated reference.

TABLE 8

Residual activity of the encapsulated lipase after storage.

| Components | Residual activity (2 weeks, 37° C.) | Stability improvement |
| --- | --- | --- |
| I: Lupasol G100 | 26% | 3 |
| II: Lupasol G100 + 1% DETA | 71% | 9 |
| III: Lupasol G100 + 1% MEA | 45% | 6 |
| IV: Lupasol G100 + 1% DEA | 92% | 12 |
| V: Lupasol G100 + 1% L-TETA | 70% | 9 |
| VI: Lupasol G100 + 1% DPTA | 40% | 5 |
| Non-encapsulated reference | 8% | 1.0 |

The results in Table 8 demonstrate that small amines can be added to improve the enzymatic stability in laundry detergent.

Example 4

Improved Long Term Enzyme Stability by Addition of Different Small Amine

Aqueous phase solutions I to V were prepared by mixing an aqueous solution of Lipase1 (120 mg active enzyme per gram) with a polybranched polyamine from Table 1 and a small amine from Table 2, according to the experimental setup shown in Table 9.

TABLE 9

Experimental setup.

| | Components in aqueous phase | | | | |
| --- | --- | --- | --- | --- | --- |
| | I (g) | II (g) | III (g) | IV (g) | V (g) |
| Lipase1 solution, 120 mg/g | 41 | 41 | 41 | 41 | 41 |
| Lupasol G100 (50% in water) | 8 | 8 | 8 | 8 | 8 |
| DETA | 0.5 | 0 | 0 | 0 | 0 |
| MEA | 0 | 0.5 | 0 | 0 | 0 |
| DEA | 0 | 0 | 0.5 | 0 | 0 |
| L-TETA | 0 | 0 | 0 | 0.5 | 0 |
| Water | | | Ad 50 g | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 µm and 150 µm.

A reactant oil phase was prepared by dissolving 28 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from Exxon Mobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 30° C. for 12 week (long term conditions).

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 10. The stability improvements were calculated relative to the non-encapsulated reference.

TABLE 10

Residual activity of the encapsulated lipase after storage.

| Components | Residual activity (12 weeks at 30° C.) | Stability improvement |
| --- | --- | --- |
| I: Lupasol G100 + 1% DETA | 55% | 32 |
| II: Lupasol G100 + 1% MEA | 36% | 21 |
| III: Lupasol G100 + 1% DEA | 51% | 30 |
| IV: Lupasol G100 + 1% L-TETA | 55% | 32 |
| V: Lupasol G100 | 3% | 2 |
| Non-encapsulated reference | 2% | 1.0 |

The results in Table 10 demonstrate that small amines can be added to different polymers and improve the long term enzymatic stability in laundry detergent Example 5

Improved Enzyme Stability by Combination of Different Small Amine and Polybranched Polyamine Compared to Single Components with Lupasol G100

Aqueous phase solutions I to V were prepared by mixing an aqueous solution of Lipase1 (120 mg active enzyme per gram) with a polybranched polyamine from Table 1 and a small amine from Table 2, according to the experimental setup shown in Table 11.

TABLE 11

Experimental setup.

| | Components in aqueous phase | | | | |
|---|---|---|---|---|---|
| | I (g) | II (g) | III (g) | IV (g) | V (g) |
| Lipase1 solution, 120 mg/g | 25 | 25 | 25 | 25 | 25 |
| Lupasol G100 (50% in water) | 0 | 2 | 4 | 6 | 8 |
| DETA | 0.5 | 0.5 | 0.5 | 0.5 | 0.5 |
| Water | | | Ad 50 g | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 µm and 150 µm.

A reactant oil phase was prepared by dissolving 28 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from Exxon Mobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 37° C. for 8 week.

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 12. The stability improvements were calculated relative to the non-encapsulated reference.

TABLE 12

Residual activity of the encapsulated lipase after storage.

| Components | Weight ratio of Lupasol G100/ DETA | Residual activity (8 weeks, 37° C.) | Stability improvement |
|---|---|---|---|
| I: 1% DETA | 0 | 0.6% | 1.2 |
| II: 2% Lupasol G100 + 1% DETA | 2 | 9% | 18 |
| III: 4% Lupasol G100 + 1% DETA | 4 | 39% | 78 |
| IV: 6% Lupasol G100 + 1% DETA | 6 | 47% | 94 |
| V: 8% Lupasol G100 + 1% DETA | 8 | 44% | 88 |
| Non-encapsulated reference | — | 0.5% | 1.0 |

The results demonstrate that the combination of small amine and polybranched PEI gives better stability than small amines alone. And furthermore that increasing the polybranched PEI level improves the stability for fixed amount of small amine; preferable above 0% PEI, more preferable above 2%, more preferable above 4%.

Example 6

Improved Enzyme Stability by Combination of Different Small Amine and Polybranched Polyamine Compared to Single Components with Epomin SP-012

Aqueous phase solutions I to VII were prepared by mixing an aqueous solution of Lipase1 (120 mg active enzyme per gram) with a polybranched polyamine from Table 1 and a small amine from Table 2, according to the experimental setup shown in Table 13.

TABLE 13

Experimental setup.

| Components in aqueous phase | I (g) | II (g) | III (g) | IV (g) | V (g) | VI (g) | VII (g) |
|---|---|---|---|---|---|---|---|
| Lipase1 solution, 120 mg/g | 25 | 25 | 25 | 25 | 25 | 25 | 25 |
| Epomin SP-012 (99+% in water) | 0 | 2 | 3 | 4 | 3 | 3 | 3 |
| DETA | 0.5 | 0 | 0 | 0 | 0.5 | 0 | 0 |
| MEA | 0 | 0 | 0 | 0 | 0 | 0.5 | 0 |
| L-TETA | 0 | 0 | 0 | 0 | 0 | 0 | 0.5 |
| Water | | | | Ad 50 g | | | |

An oil phase was prepared by mixing 1000 mL of a paraffinic oil (Whiteway 15 supplied by Statoil) with 60 g of a 20% solution of high-MW hydrolyzed copolymer of styrene, stearyl methacrylate and maleic anhydride terpolymer emulsifier in paraffinic oil by stirring (see WO 99/01534, Example 5).

Each of the aqueous phases was added to 100 mL oil phase under stirring to form water-in-oil emulsions having a mean droplet size between 50 µm and 150 µm.

A reactant oil phase was prepared by dissolving 28 g of Isophthaloyl chloride (from Sigma Aldrich) with ad 700 g paraffinic oil and heating to 85° C. with continuous magnetic stirring.

To each of the water-in-oil emulsions, 50 mL hot reactant oil phase was added to initiate the interfacial polymerization reaction and capsule formation. The reaction was allowed to complete for 1 hour with stirring.

Capsules were then allowed to settle for approximately 5 minutes, the supernatant discarded and the capsules rinsed with paraffinic oil (Whiteway 15 from Statoil; or Isopar M from Exxon Mobil). The final capsule product was drained for oil as much as possible.

Each batch of capsules was mixed with 100 mL Detergent B.

A reference was prepared by mixing 0.2 g of the Lipase1 solution (120 mg active enzyme per gram) with 125 g Detergent B with magnetic stirring.

Reference and capsule batches were split into closed vials with approximately 7 g in each and stored at 5° C. or 37° C. for 2 week (accelerated conditions).

After storage, the activity was measured by using standard enzyme analytical methods (hydrolysis of p-nitrophenyl palmitate at 37° C., pH=8.0) after an initial 1:100 dilution in demineralized water to facilitate release of enzyme from the capsules. Residual activities were calculated relative to the samples stored at 5° C. The results are shown in Table 14. The stability improvements were calculated relative to the non-encapsulated reference.

TABLE 14

Residual activity of the encapsulated lipase after storage.

| Components | Residual activity (2 weeks, 40° C.) | Stability improvement |
|---|---|---|
| I: 1% DETA | 2% | 0.9 |
| II: 2% Epomin SP-012 | 6% | 2 |
| III: 4% Epomin SP-012 | 6% | 2 |
| IV: 6% Epomin SP-012 | 6% | 2 |
| V: 6% Epomin SP-012 + 1% DETA | 65% | 23 |
| VI: 6% Epomin SP-012 + 1% MEA | 25% | 9 |
| VII: 6% Epomin SP-012 + 1% L-TETA | 73% | 24 |
| Non-encapsulated reference | 3% | 1.0 |

The results demonstrate that the combination of small amine and polybranched PEI gives better stability than small amines alone and polybranched PEI alone.

The invention claimed is:

1. A microcapsule composition, comprising a compound entrapped in a compartment formed by a membrane, which membrane is produced by cross-linking of (a) a polybranched polyamine having a molecular weight of more than 800 Da, and (b) an aliphatic or aromatic amine having a molecular weight of less than 300 Da;
wherein the weight ratio of (a)/(b) is in the range of 0.1 to 1000.

2. The composition of claim 1, wherein the compound is an enzyme.

3. The composition of claim 2, wherein the enzyme is selected from the group consisting of protease, metalloprotease, subtilisin, amylase, lipase, cutinase, cellulase, mannanase, pectinase, xanthanase, DNAse, laccase, peroxidase, haloperoxidase, perhydrolase, and combinations thereof; preferably the enzyme is a lipase.

4. The composition of claim 1, wherein the reactive amino groups of the polybranched polyamine constitute at least 15% of the molecular weight.

5. The composition of claim 1, wherein the diameter of the compartment is at least 50 micrometers.

6. The composition of claim 1, wherein the compartment contains at least 1% active enzyme by weight of the total compartment.

7. The composition of claim 1, which further includes an alcohol, such as a polyol.

8. The composition of claim 1, wherein (a) is a polybranched polyethyleneimine having more than two branching points and more than two reactive amino groups.

9. The composition of claim 1, wherein (b) is an ethyleneamine or alkanolamine.

10. The composition of claim 1, wherein (b) is selected from the group consisting of ethylene diamine, diethylene triamine, triethylene tetraamine, bis(3-aminopropyl)amine, monoethanolamine, diethanolamine, triethanolamine, hexamethylene diamine, diamino benzene, piperazine, and tetraethylene pentamine.

11. The composition of claim 1, wherein (b) is selected from the group consisting of diethylene triamine, triethylene tetraamine, bis(3-aminopropyl)amine, monoethanolamine, and diethanolamine.

12. The composition of claim 1, wherein the compartment comprises a source of Mg2+, Ca2+, or Zn2+ ions, such as a poorly soluble salt of Mg2+, Ca2+, or Zn2+.

13. The composition of claim 1, wherein the membrane is produced by using an acid chloride as crosslinking agent, such as isophtaloyl chloride, terephthaloyl chloride, or trimesoyl chloride.

14. The composition of claim 1, wherein the membrane is produced by interfacial polymerization.

15. A liquid detergent composition, comprising a surfactant and/or a detergent builder, and the microcapsule composition of claim 1.

16. The composition of claim 15, which comprises at least two mutually incompatible or reactive components, wherein one of the components is entrapped in the compartment of the microcapsule, and the other component is not entrapped in the compartment of the microcapsule.

17. A method for preparing the microcapsule composition of claim 1, comprising entrapping a compound in a compartment formed by a membrane, which membrane is produced by cross-linking of (a) a polybranched polyamine having a molecular weight of more than 800 Da, and (b) an aliphatic or aromatic amine having a molecular weight of less than 300 Da; wherein the weight ratio of (a)/(b) is in the range of 0.1 to 1000.

* * * * *

SEQUENCE LISTING

<160> NUMBER OF SEQ ID NOS: 10

<210> SEQ ID NO 1
<211> LENGTH: 269
<212> TYPE: PRT
<213> ORGANISM: Artificial
<220> FEATURE:
<223> OTHER INFORMATION: Thermomyces lanuginosus lipase variant

<400> SEQUENCE: 1

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Arg Ala Pro Ala Gly Thr
            20                  25                  30

Asn Ile Thr Cys Thr Ala Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Glu
                85                  90                  95

Leu Lys Glu Ile Asn Asp Ile Cys Ser Gly Cys Arg Gly His Ala Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Lys Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Arg Arg Arg Asp Ile Val Lys Ile Glu Gly
225                 230                 235                 240
```

```
        Ile Asp Ala Thr Gly Gly Asn Asn Gln Pro Asn Ile Pro Ser Ile Thr
                        245                 250                 255

Ala His Leu Trp Tyr Phe Gly Leu Ile Gly Thr Cys Leu
                    260                 265

<210> SEQ ID NO 2
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Leu
<220> FEATURE:
<221> NAME/KEY: MISC_FEATURE
<222> LOCATION: (4)..(4)
<223> OTHER INFORMATION: Tyr-H

<400> SEQUENCE: 2

Leu Gly Ala Tyr
1

<210> SEQ ID NO 3
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Phe
<220> FEATURE:
<221> NAME/KEY: MISC_FEATURE
<222> LOCATION: (4)..(4)
<223> OTHER INFORMATION: Tyr-H

<400> SEQUENCE: 3

Phe Gly Ala Tyr
1

<210> SEQ ID NO 4
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Tyr
<220> FEATURE:
<221> NAME/KEY: MISC_FEATURE
<222> LOCATION: (4)..(4)
<223> OTHER INFORMATION: Tyr-H

<400> SEQUENCE: 4

Tyr Gly Ala Tyr
1

<210> SEQ ID NO 5
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
```

```
<223> OTHER INFORMATION: Acetyl-Phe; MeO-CO-Phe; MeSO2-Phe; or EtSO2-Phe
<220> FEATURE:
<221> NAME/KEY: MISC_FEATURE
<222> LOCATION: (4)..(4)
<223> OTHER INFORMATION: Leu-H

<400> SEQUENCE: 5

Phe Gly Ala Leu
1

<210> SEQ ID NO 6
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Phe or MeO-CO-Phe
<220> FEATURE:
<221> NAME/KEY: MISC_FEATURE
<222> LOCATION: (4)..(4)
<223> OTHER INFORMATION: Tyr-H

<400> SEQUENCE: 6

Phe Gly Ala Phe
1

<210> SEQ ID NO 7
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Phe
<220> FEATURE:
<221> NAME/KEY: MISC_FEATURE
<222> LOCATION: (4)..(4)
<223> OTHER INFORMATION: Tyr-H

<400> SEQUENCE: 7

Phe Gly Val Tyr
1

<210> SEQ ID NO 8
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Phe
<220> FEATURE:
<221> NAME/KEY: MISC_FEATURE
<222> LOCATION: (4)..(4)
<223> OTHER INFORMATION: Met-H

<400> SEQUENCE: 8

Phe Gly Ala Met
1

<210> SEQ ID NO 9
<211> LENGTH: 4
<212> TYPE: PRT
<213> ORGANISM: Artificial
```

```
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: Acetyl-Trp
<220> FEATURE:
<221> NAME/KEY: MISC_FEATURE
<222> LOCATION: (4)..(4)
<223> OTHER INFORMATION: Tyr-H

<400> SEQUENCE: 9

Trp Leu Val Tyr
1

<210> SEQ ID NO 10
<211> LENGTH: 4
<212> TYPE: PRT
<213> ORGANISM: Artificial
<220> FEATURE:
<223> OTHER INFORMATION: Subtilisin inhibitor
<220> FEATURE:
<221> NAME/KEY: MISC_FEATURE
<222> LOCATION: (1)..(1)
<223> OTHER INFORMATION: MeO-P(OH)(O)-Leu
<220> FEATURE:
<221> NAME/KEY: MISC_FEATURE
<222> LOCATION: (4)..(4)
<223> OTHER INFORMATION: Leu-H

<400> SEQUENCE: 10

Leu Gly Ala Leu
1
```